(12) United States Patent
Clark et al.

(10) Patent No.: US 8,876,798 B2
(45) Date of Patent: Nov. 4, 2014

(54) CATHETER ADAPTER

(75) Inventors: Geoff Clark, Lempster, NH (US); Christian Schlerf, Keene, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 1292 days.

(21) Appl. No.: 12/659,020

(22) Filed: Feb. 23, 2010

(65) Prior Publication Data
US 2011/0208132 A1    Aug. 25, 2011

(51) Int. Cl.
| | |
|---|---|
| A61M 25/16 | (2006.01) |
| A61M 25/18 | (2006.01) |
| A61M 39/00 | (2006.01) |
| A61M 39/10 | (2006.01) |
| A61M 5/00 | (2006.01) |
| A61M 39/12 | (2006.01) |
| A61M 25/00 | (2006.01) |

(52) U.S. Cl.
CPC ....... *A61M 39/12* (2013.01); *A61M 2039/1027* (2013.01); *A61M 39/1011* (2013.01); *A61M 25/0097* (2013.01); *A61M 2039/1077* (2013.01)
USPC ............ 604/533; 604/257; 604/534; 604/535

(58) Field of Classification Search
USPC ...... 128/DIG. 6, DIG. 26; 604/174, 177, 533, 604/534, 535, 538, 257
See application file for complete search history.

(56) References Cited

U.S. PATENT DOCUMENTS

| | | | |
|---|---|---|---|
| 4,006,744 A | | 2/1977 | Steer |
| 4,397,647 A | * | 8/1983 | Gordon .......................... 604/180 |
| 4,675,007 A | * | 6/1987 | Terry ............................. 604/533 |
| 4,723,948 A | | 2/1988 | Clark et al. |
| 4,950,255 A | | 8/1990 | Brown et al. |
| 5,053,015 A | | 10/1991 | Gross |
| 5,078,703 A | * | 1/1992 | Bryant .......................... 604/533 |
| 5,127,626 A | | 7/1992 | Hilal et al. |
| 5,211,637 A | | 5/1993 | Goto et al. |
| 5,312,337 A | | 5/1994 | Flaherty et al. |
| 5,405,339 A | | 4/1995 | Kohnen et al. |
| 5,702,371 A | | 12/1997 | Bierman |
| 6,099,519 A | | 8/2000 | Olsen et al. |
| 6,217,564 B1 | | 4/2001 | Peters et al. |
| 6,254,589 B1 | | 7/2001 | Raoz |
| 6,350,260 B1 | | 2/2002 | Goebel et al. |
| 6,524,304 B1 | | 2/2003 | Picou et al. |

(Continued)

OTHER PUBLICATIONS

International Search Report and Written Opinion (PCT/2011/00287), Oct. 31, 2011, ISA/KR.

*Primary Examiner* — Kevin C Sirmons
*Assistant Examiner* — Shefali Patel
(74) *Attorney, Agent, or Firm* — Louis Woo

(57) ABSTRACT

A clam shell shaped adapter for retaining a catheter to establish a fluid path between the catheter and a fluid device or line has first and second shells integrally connected by a living hinge. The first shell has a luer end and a catheter end. A flexible tubing at an inner surface of the first shell connects the luer end to the catheter end. The catheter is inserted through the catheter end to extend along the flexible tubing. A retainer structure is provided at an inner surface of the second shell so that when the first and second shells close upon each other, the retainer structure presses against the flexible tubing to fixedly retain the catheter in a fluidly sealing manner. Respective latch mechanisms provided at the shells lockingly couple the first and second shells to each other.

20 Claims, 7 Drawing Sheets

(56) References Cited

U.S. PATENT DOCUMENTS

| | | |
|---|---|---|
| 6,676,652 B2 | 1/2004 | Mogg |
| 7,044,936 B2 | 5/2006 | Harding |
| 7,344,527 B2 | 3/2008 | Schweikert et al. |
| 7,481,796 B2 | 1/2009 | Nishtala et al. |
| 7,571,889 B2 | 8/2009 | Miyahara |
| 7,635,354 B2 | 12/2009 | Navarro |
| 7,635,355 B2 | 12/2009 | Bierman |
| 2002/0151838 A1 | 10/2002 | Beck et al. |
| 2004/0162544 A1* | 8/2004 | Raulerson et al. ............ 604/533 |
| 2005/0209581 A1 | 9/2005 | Butts et al. |
| 2006/0015086 A1 | 1/2006 | Rasmussen et al. |
| 2006/0271000 A1 | 11/2006 | Randelletta et al. |
| 2007/0088329 A1 | 4/2007 | Bierman |
| 2007/0225683 A1 | 9/2007 | Raulerson et al. |
| 2008/0183154 A1 | 7/2008 | Racz et al. |
| 2008/0294146 A1 | 11/2008 | Charlez |
| 2009/0187165 A1 | 7/2009 | Kaern |
| 2009/0204105 A1 | 8/2009 | Johansson et al. |
| 2009/0270842 A1 | 10/2009 | Blocher et al. |
| 2009/0292273 A1 | 11/2009 | Racz et al. |

\* cited by examiner

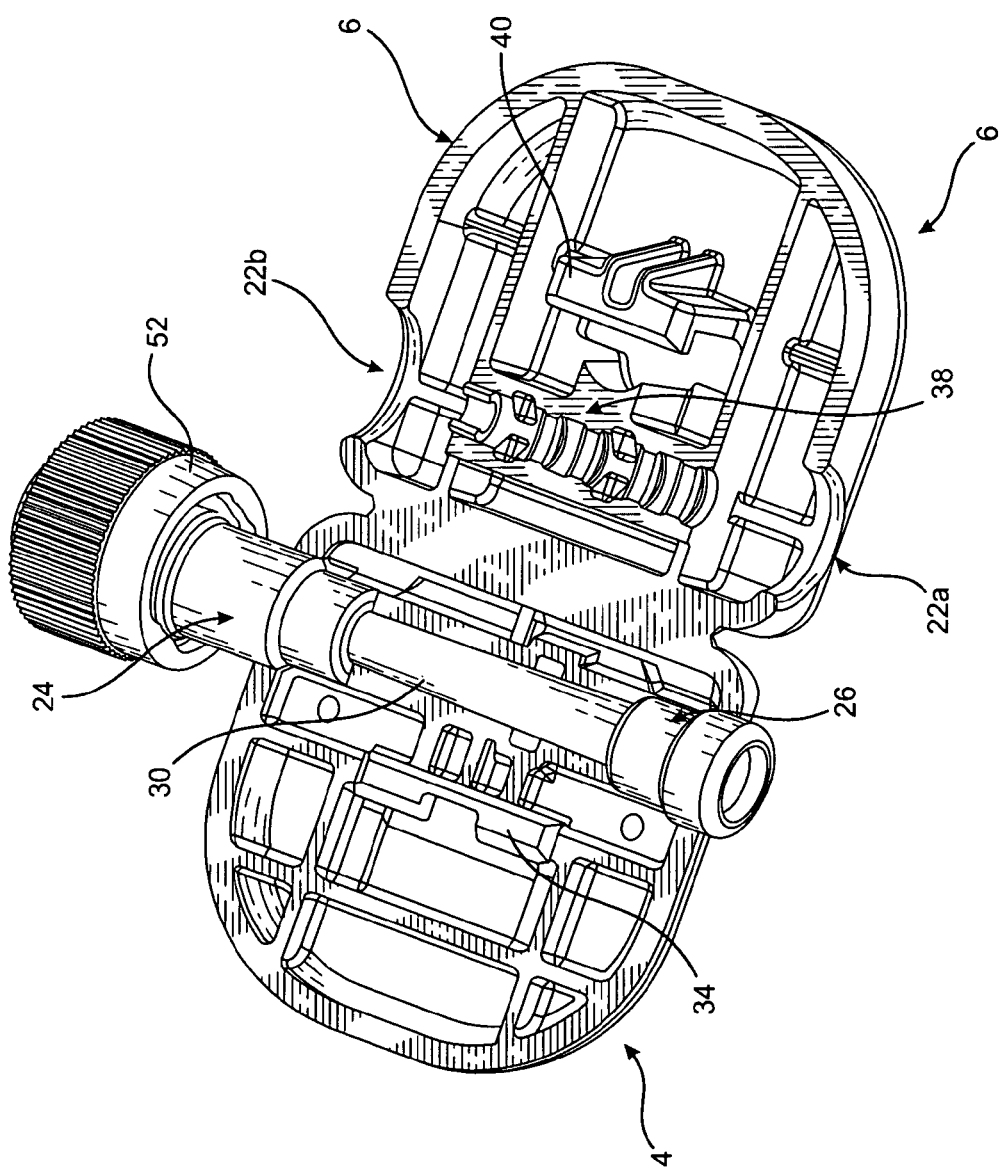

CATHETER ADAPTER

FIELD OF THE INVENTION

The present invention relates to a medical device for coupling a catheter to a fluid delivery or storage device, and more particularly to an adapter for connecting a catheter to a fluid delivery or storage device that has its latching mechanisms remotely located from the exterior surfaces of the adapter to prevent accidental uncoupling of the catheter.

BACKGROUND OF THE INVENTION

Catheter connector devices for coupling a catheter to a fluid delivery or storage device such as a syringe or a medicament fluid line is known. Such devices may be used for medical procedures including an epidural injection procedure whereby a catheter is inserted into a patient's epidural space so that medicament may be injected to the patient to locally anesthesize the patient for example during child birth. Before an epidural catheter can be inserted into the epidural space of the patient, an epidural needle is first inserted into the epidural space. Thereafter an epidural catheter is guided by the needle into the epidural space of the patient and the epidural needle is removed. A catheter connector device then connects the free end of the catheter to a syringe, a fluid line or other fluid store means that has the medicament. The prior art medical catheter connector devices would clamp the catheter and provide an end whereby the luer of the syringe, fluid line or other fluid store means may be connected so that a fluid path is established between the catheter and the syringe, fluid line or other fluid store means. Some prior art catheter connectors are disclosed in U.S. Pat. Nos. 5,078,703, 4,006,744, 6,350,260, 7,635,355, and U.S. publication Nos. 2006/0271000, 2008/0183154.

Most, if not all of the noted patents and publications disclose devices having locking mechanisms that are exposed, so that there may be accidental uncoupling of the catheter. The others of those disclosed devices require the relative twisting and turning of portions of the devices to align the catheter with the fluid store means, if the fluid store means happens to be a fluid line.

The instant invention catheter adapter overcomes the disadvantages of the prior art catheter connectors.

SUMMARY OF THE PRESENT INVENTION

The medical adapter of the instant invention is a one piece clam shell shaped device made of medical plastics such as polypropylene that includes two shells that are integrally connected by a common living hinge. The shells have counter matching peripheries so that when folded along the living hinge with their respective inner surfaces facing each other or in opposed relationship to each other, the peripheries of the shells matchingly abut. The shells are formed such that one of the shells is thinner than the other. The thinner shell has molded thereat a luer end at one end and an aperture end for accepting a catheter at its other end along a longitudinal axis that runs parallel and adjacent to the living hinge. An elastomeric flexible tubing or tube connects the luer end to the aperture end at the inner surface of the thinner shell so that a through path is established between the luer end and the aperture end. As the flexible tube connected luer and aperture ends are aligned adjacent to the living hinge, they are positioned offset from the center of the shell.

At the approximate center of the thinner shell that has the luer and aperture ends, there is formed at the inner surface a latch mechanism that comprises a catch.

At the other shell, which is the thicker of the two shells, of the medical device of the instant invention there is formed at approximately the center thereof at its inner surface another latch mechanism in the form of a finger that would snappingly grasp the catch at the other shell, when the two shells are movingly folded along the living hinge towards each other. When the shells are closed onto each other with their respective peripheries matchingly abut, the two shells are firmly engaged to each other due to the finger at the thicker shell lockingly coupled to the catch at the thinner shell. When thus coupled, a retainer surface structure at the inner surface of the thicker shell presses against the flexible tubing at the inner surface of the thinner shell to fixedly hold or retain the catheter that has been inserted through the aperture end into the flexible tubing.

A notch or cavity to enable the decoupling of the shells is provided from the outer surface to the interior of the shell that has the latch finger. A pointed object such as a conventional male luer slip end of a syringe can be inserted into the notch to push against a boss at the back of the finger to disengage the finger from the catch, to thereby decouple the two shells and remove the pressure applied to the flexible tubing by the retainer structure. The catheter inserted to and extending along the flexible tubing could then be withdrawn from the device.

Another feature of the instant invention device is that the formation of the flexible tubing is by injection molding an elastomeric material through a bore at the outer surface of the thinner shell so that the injected elastomeric material would congeal to form the flexible tubing that connects the luer fitting end to the aperture end. During the injection molding process, a soft elastomeric pad that enhances the ease with which a user can grasp the adapter is formed at the outer surface of the shell.

The present invention therefore relates to a one piece catheter connector device that comprises a first member or one shell and a second member or an other shell each having an inner surface and an outer surface. The one and other shells are integrally connected at a common living hinge and have respective matching peripheries to form a clam shell shaped member. The one shell has formed thereat a luer end and an aperture end connected by a flexible tubing at its inner surface so that a through passage is established between the luer end and the aperture end. The aperture end is adapted to accept a catheter input to said flexible tubing. The one shell has a first latch mechanism at its approximate center and the other shell has a second latch mechanism at its approximate center that lockingly engage to couple the one and other shells to each other when the one and other shells are folded along the common living hinge to move the respective inner surfaces of the one and other shells to face each other. The other shell includes a retainer structure at its inner surface that presses against the flexible tubing to fixedly hold or retain the catheter in the flexible tubing when the one and other shells are coupled to each other.

The instant invention also relates to an adapter for coupling a catheter to a fluid store or a fluid line that comprises a one piece clam shell shaped member having one shell and other shell integrally attached to and foldable toward each other by a living hinge. The one shell and other shell each have an inner surface and an outer surface. The one shell has formed thereat a luer end and an aperture end connected by a flexible tubing at its inner surface so that a through passage is established between the luer end and the aperture end. The aperture end is adapted to accept a catheter input to said flexible tubing. A first latch mechanism at approximately the center of the one shell lockingly engages a second latch mechanism at approximately the center of the other shell when the one and other shells are folded along the living hinge to close upon each other. A retainer structure at the inner surface of the other shell presses against the flexible tubing to fixedly hold or retain the catheter in the flexible tubing when the first and second latch mechanisms are engaged to each other.

The instant invention is further related to an apparatus that comprises a catheter, a fluid store means; and an adapter that includes a one piece clam shell shaped member having one shell and other shell integrally attached to and foldable toward each other by a living hinge. The one shell and the other shell each have an inner surface and an outer surface. The one shell has formed thereat a luer end and an aperture end connected by a flexible tubing at its inner surface so that a through passage is established between the luer end and the aperture end. The aperture end is adapted to accept the catheter into the flexible tubing and the luer end is adapted to mate with a counterpart luer at the fluid store means. A first latch mechanism at the one shell lockingly engages a second latch mechanism at the other shell when the one and other shells are folded along the living hinge to close upon each other. A retainer structure at the inner surface of the other shell presses against the flexible tubing to fixedly hold or retain the catheter when the first and second latch mechanisms are engaged to each other, whereby a fluid path between the catheter and the fluid store means is established by the adapter.

BRIEF DESCRIPTION OF THE FIGURES

The present invention will become apparent and the invention itself will be best understood by reference to the following description of the present invention taken injunction with the accompanying drawings, wherein:

FIG. 10 corresponds to FIG. 2 but with the luer end threadedly mated to a protective cover cap.

DETAILED DESCRIPTION OF THE INVENTION

Figure 9:
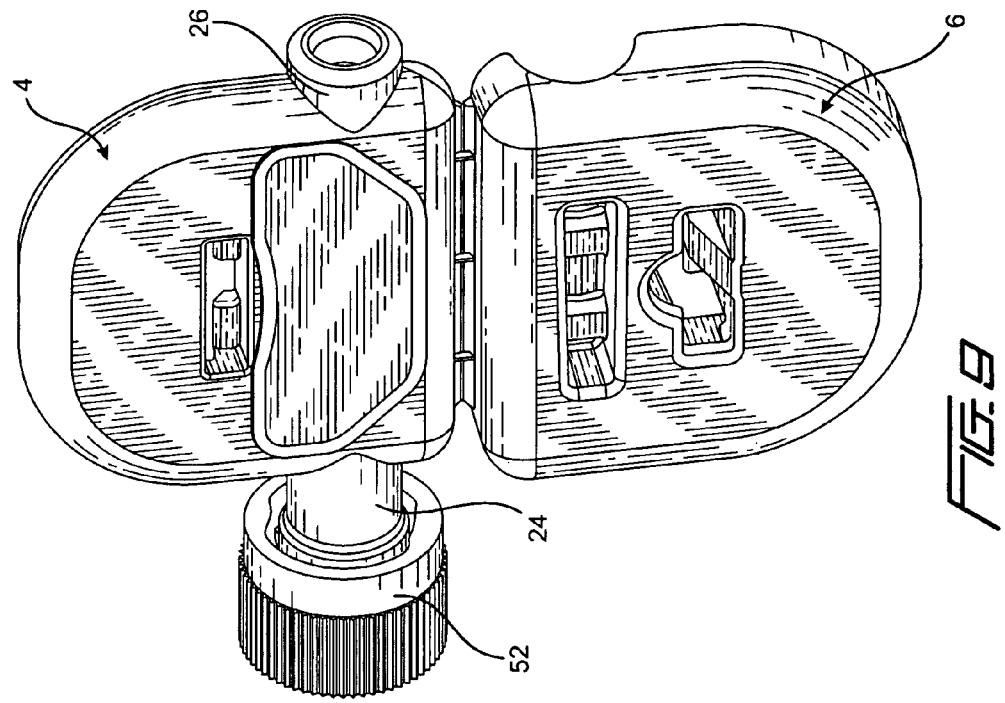
FIG. 9 is a perspective view of the outer surfaces of both shells of the device lying a coplanar relationship, with the luer end threadedly mated to a protective cover cap.

With reference to FIGS. 1-5, the medical catheter adapter 2 of the instant invention is a combination coupler and retainer device for connecting a catheter, for example an epidural catheter, to a fluid storage or fluid delivery device such as a syringe and a fluid line. In particular, device 2 is shown to be a single unitary device in the shape of a clam shell that has a first member or one shell 4 and a second member or other shell 6 integrally connected by a common living hinge 8 so that the shells are movable relative towards each other per the directions designated by directional arrows 10 and 12 to close upon each other in the closed position per shown in FIG. 3.

Figure 1:
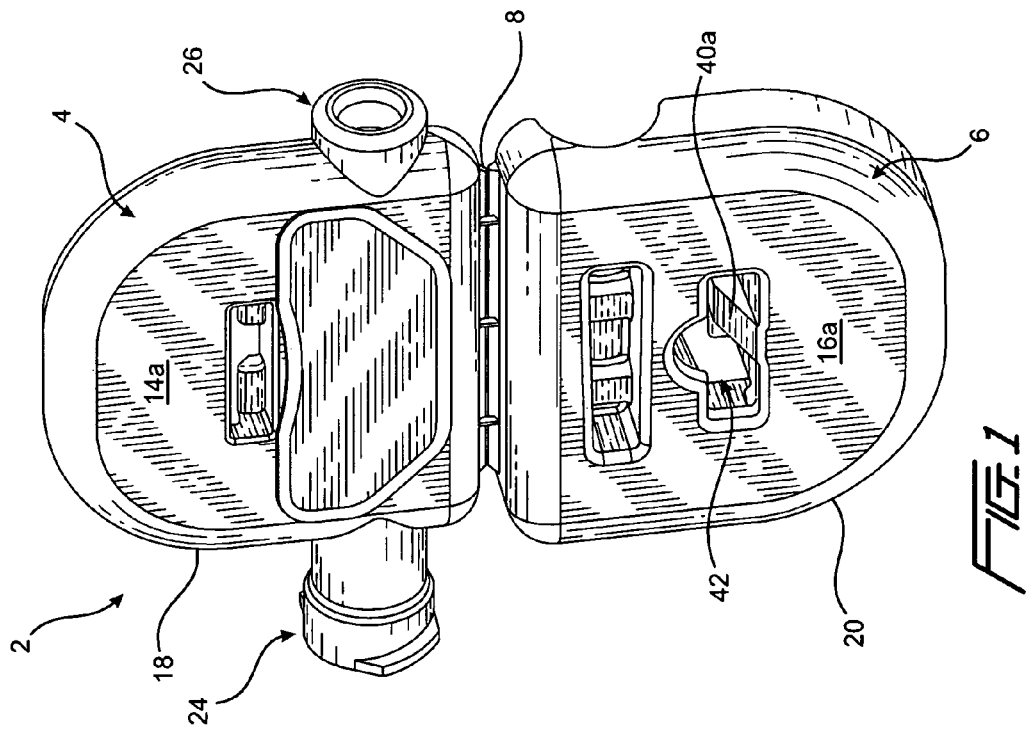
FIG. 1 is a perspective view of the catheter adapter coupling device of the instant invention showing both shells of the device along the same plane.
Figure 2:
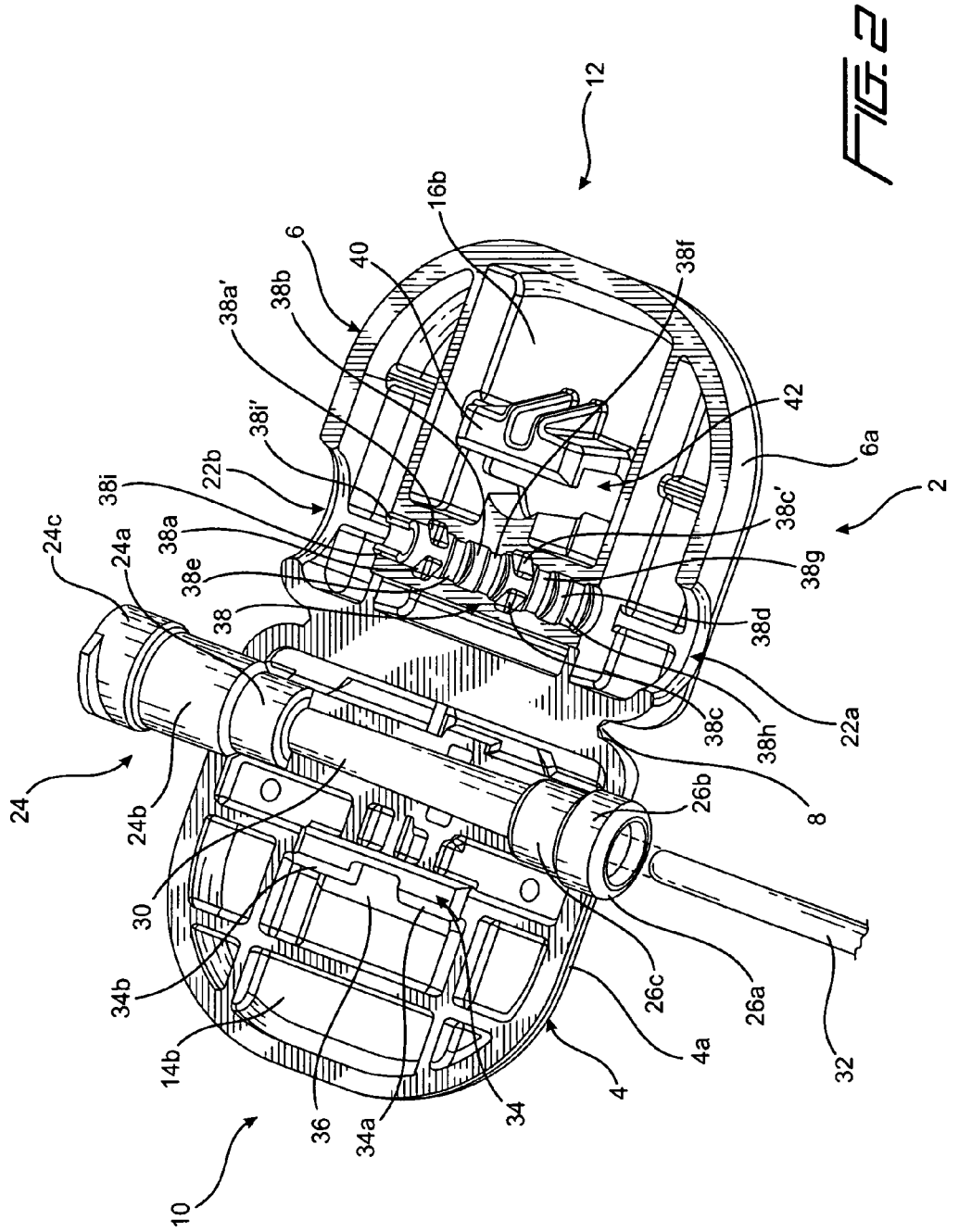
FIG. 2 shows the device of FIG. 1 with the inner surfaces of both shells of the device exposed along the same plane.
Figure 3:
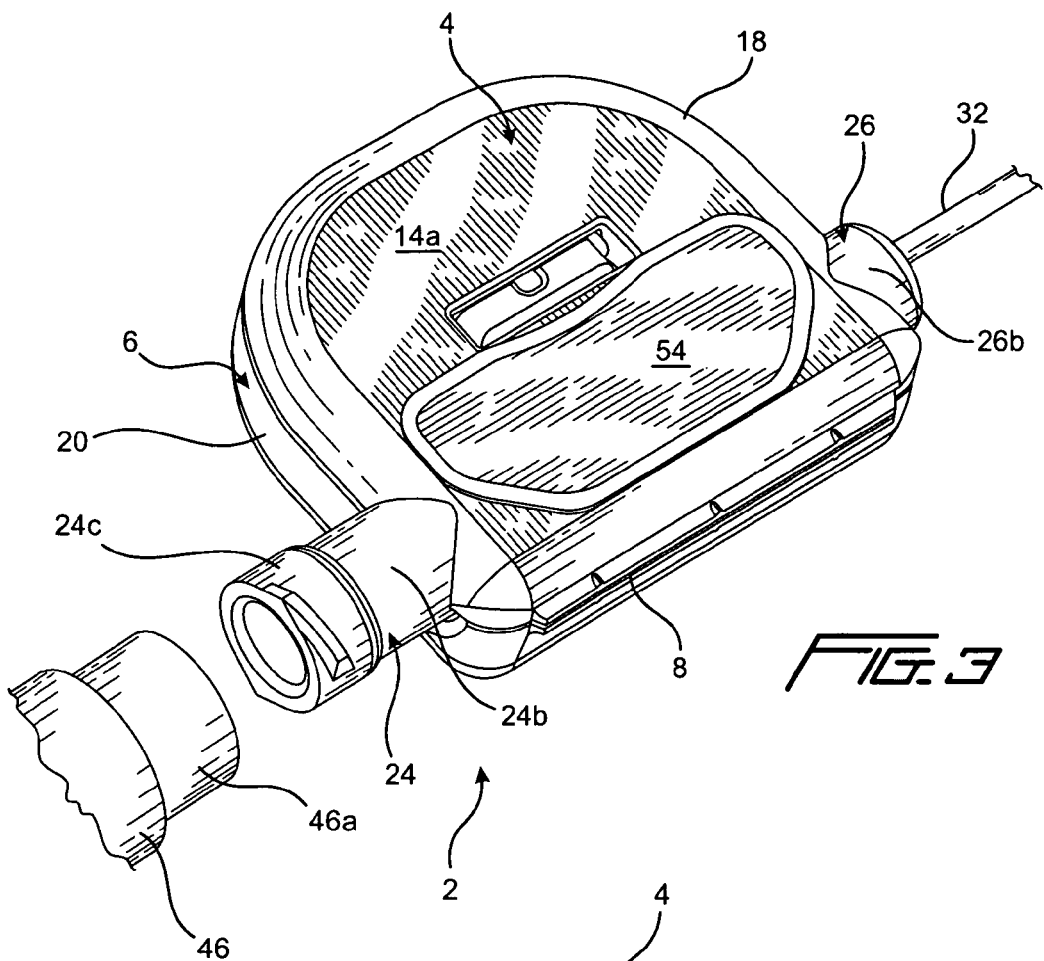
FIG. 3 shows the device of the instant invention with both shells of the device closed upon each other to form a closed and/or coupled device.

As shown in FIGS. 1 and 2, shell 4 has an outer surface 14a and an inner surface 14b, while shell 6 has an outer surface 16a and an inner surface 16b. For the most part, the peripheries 18 and 20 of shells 4 and 6, respectively, have counterpart matching configurations, so that when device 2 is in the closed position as shown in FIG. 3, peripheries 18 and 20 matchingly abut to form a closed container with no external edges from either of the shells showing beyond the common peripheries 18 and 20. Accordingly, the catheter adapter 2 of the instant invention, when in its closed and/or coupled position, is a compact device with a smooth boundary except for two connection ports as will be described, infra.

As shown in FIG. 2, the thickness of shell 4, designated 4a, is less than the thickness 6a of shell 6. In other words, shell 4 is a thinner shell than shell 6, which periphery 20 includes semi-circumferential openings 22a and 22b having respective curvatures that allow shells 4 and 6 to close in light of the connection ports formed at shell 4.

In particular, shell 4 has formed as a part thereof and extending mostly from its inner surface 14b two connection ports that may be referred to as a luer fitting end (or luer end) 24 and a catheter fitting aperture end (or an aperture end) 26. As device 2 comprises a one piece body that is molded of medical plastics material such as polypropylene, luer end 24 and aperture end 26 are formed at the same time that device 2 is molded so that device 2, before the injection molding of an elastomeric material thereto, is per shown in FIGS. 6 and 7.

Luer end 24 comprises a base 24a, a mid-section 24b and a fitting end 24c. The outside diameter of mid-section 24b is configured to be slightly less than the semi-circumferential opening 22b at shell 6 so that opening 22b would form fit over mid-section 24b when shells 4 and 6 are moved relative to each other per the direction shown by directional arrows 10 and 12 for closing and coupling the shells.

Aperture end 26, which may also be referred to as a catheter end, has an aperture opening 26a, a front end 26b and a base 26c. The outside diameter of front end 26b is configured to be slightly less than the semi-circumferential opening 22a of shell 6 so that opening 22a would form fit over front end 26b when shells 4 and 6 are closed per shown in FIG. 3.

To establish a through path between luer end 24 and aperture end 26, an elastomer is injection molded though a bore 28 (FIGS. 6 and 7) from the outer surface 14a of shell 4 so that an elastomeric flexible tube or tubing 30 is formed at the inner surface 14b of shell 4 for establishing a through passageway between luer end 24 and aperture end 26. Although not clearly shown, the elastomeric material extends partially into base portion 24a of luer end 24 at one end and is flush with aperture opening 26a of aperture end 26. Catheter 32, for example an epidural catheter, is insertable through aperture opening 26a into aperture end 26, and from there extends through flexible tubing 30 into base 24a of luer end 24. The insertion movement of the catheter is stopped by an internal shoulder (not shown) at the junction of base 24a and mid-section 24b of luer end 24.

Figure 7:
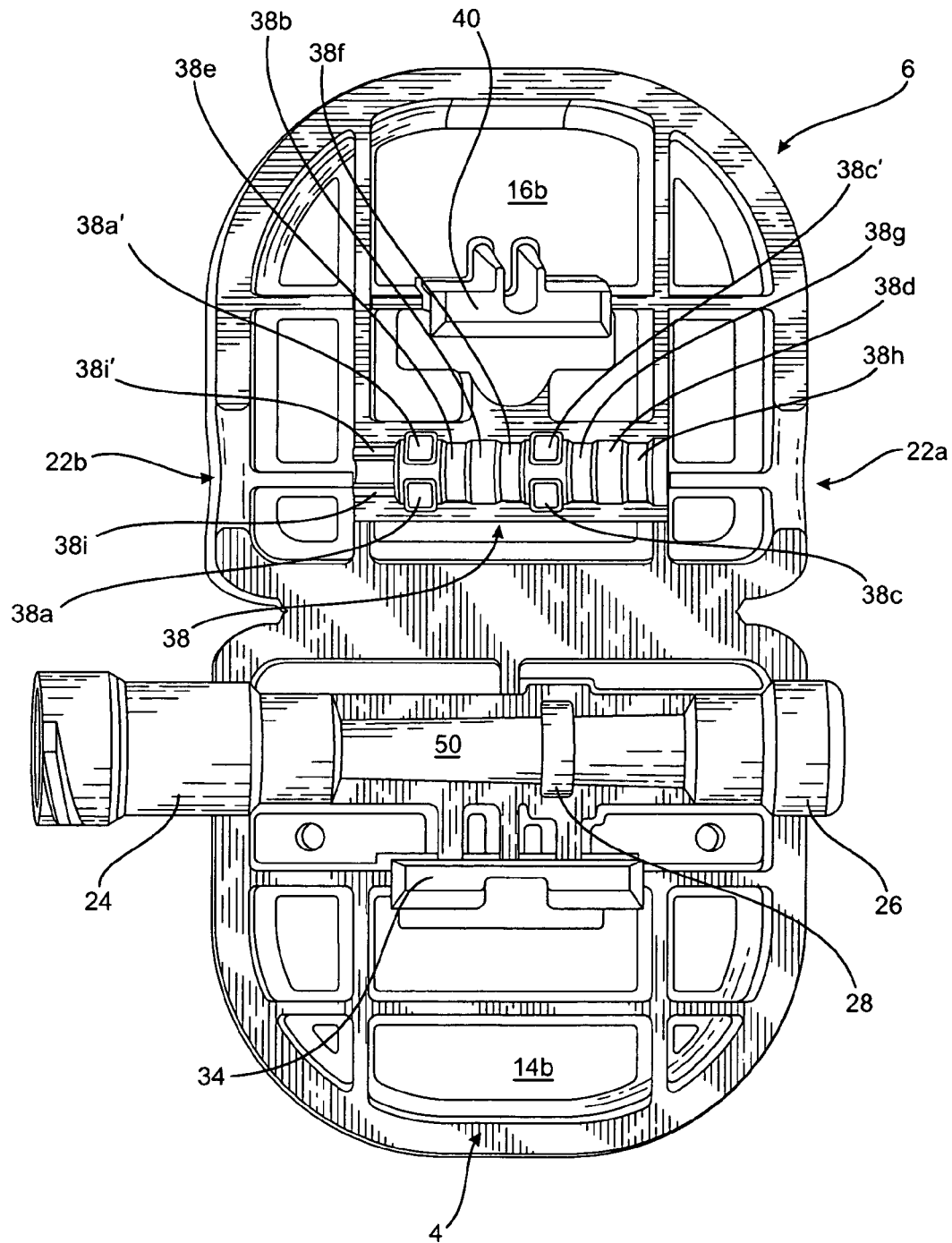
FIG. 7 is a perspective view of the inner surfaces of the two shells of the instant invention medical device before the injection molding process of forming the flexible tubing in the device

At inner surface 16b of shell 6 there is integrally formed a retainer structure 38 that has a length substantially the same as the length of the flexible tubing between base 26c of aperture end 26 and base 24a of luer fitting end 24. As illustrated in FIGS. 2 and 7, retainer structure 38 may comprises a plurality of recesses 38a and 38a', 38b, 38c and 38c', and 38d, interspaced with a plurality of ribs 38e, 38f, 38g and 38h. The respective plurality of recesses and ribs together form a ribbed surface that slightly curves inwardly towards the inner surface 16b of shell 6 for contacting flexible tubing 30. Also being part of retainer structure 38 are two spatially opposed protrusions 38i and 38i' positioned at the end of the retainer structure that is proximate to semi-circumferential opening 22b.

The ribbed surface of retainer structure 38 is configured to enable it to form fittedly press against flexible tubing 30 so that those portions of the elastomeric material of flexible tubing 30 that come into contact with the ribs are compressed by the ribs while those portions of the elastomeric material that end up being in opposed relationship to the recesses would remain substantially uncompressed so as to extend into the recesses. Thus, when shells 4 and 6 are moved to close upon each other, retainer structure 38—and in particular its ribbed contact surface formed by the protrusions 38i and 38i', the recesses 38a and 38a', 38b, 38c and 38c', and 38d, and the ribs 38e, 38f, 38g and 38h—would press against flexible tubing 30 such that there is a form fitting compressed crimping of the elastomeric material of the flexible tubing 30 by the respective recesses, ribs and protrusions of the retainer structure 38, so that catheter 32 positioned lengthwise inside flexible tubing 30 is held fixedly therein in a fluid sealingly tight relationship. Putting it differently, with the portion of retainer structure 38 that makes contact with flexible tubing 30 configured per shown in FIGS. 2 and 7, once the shells 4 and 6 are lockingly coupled to each other, as will be described infra, retainer structure 38 acts to establish a fluid tight seal between catheter 32 and flexible tubing 30 as well as to fixedly retain catheter 32 and flexible tubing 30 relative to each other. Also, the recesses, ribs and protrusions of retainer structure 38 are configured to have dimensions that ensure that there is no crimping of the catheter when retainer structure 38 compresses flexible tubing 30, so as not to impede the flow of fluid through catheter 32.

Thus, when shells 4 and 6 are moved via living hinge 8 to close upon and securely coupled to each other, per shown in FIG. 3, retainer structure 38 will press against flexible tubing 30 to fixedly hold catheter 32 along flexible tubing 30 without crimpingly distorting the through passage of catheter 32, and at the same time provide a fluid tight seal between catheter 32 and flexible tubing 30 to prevent fluid leakage from flexible tubing 30 and therefore the adapter. Catheter 32 is not removable from device 2 until shells 4 and 6 are uncoupled and disengaged from each other.

Further with respect to shell 4, formed integrally at the inner surface 14b thereof is a latch mechanism in the shape of an interrupted catch 34 that includes catch members 34a and 34b. An opening 36 connects inner surface 14b to outer surface 14a of shell 4.

Figure 5:
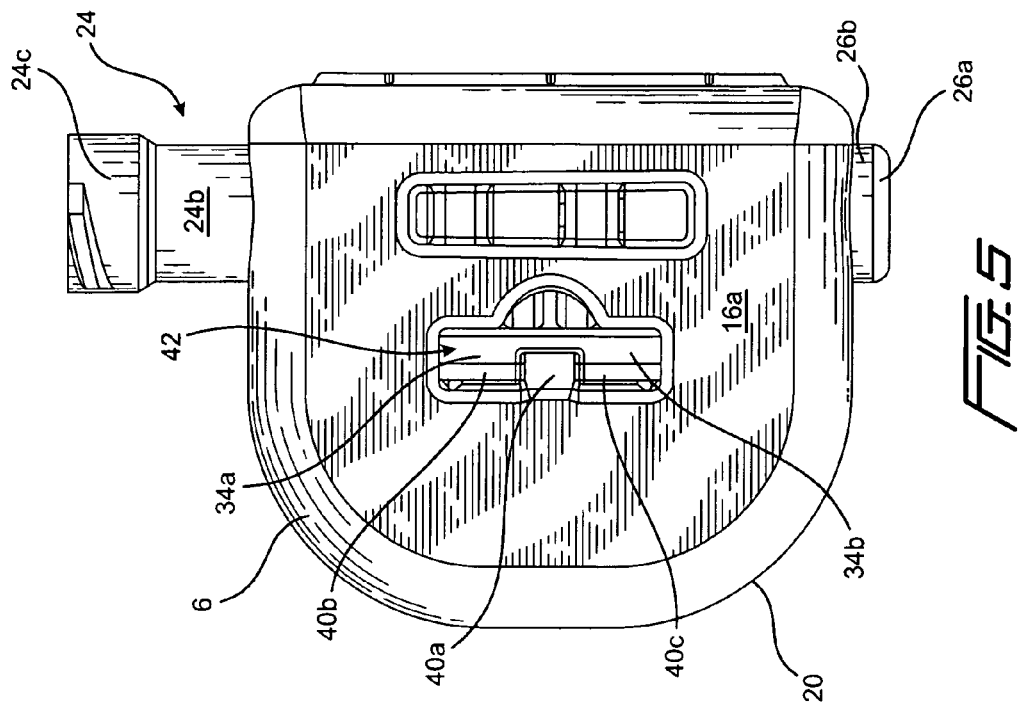
FIG. 5 is a plan view of the outer surface of the other shell of the device of the instant invention showing a notch or cavity that exposes the boss of the finger latch mechanism located at the interior of the device.
Figure 6:
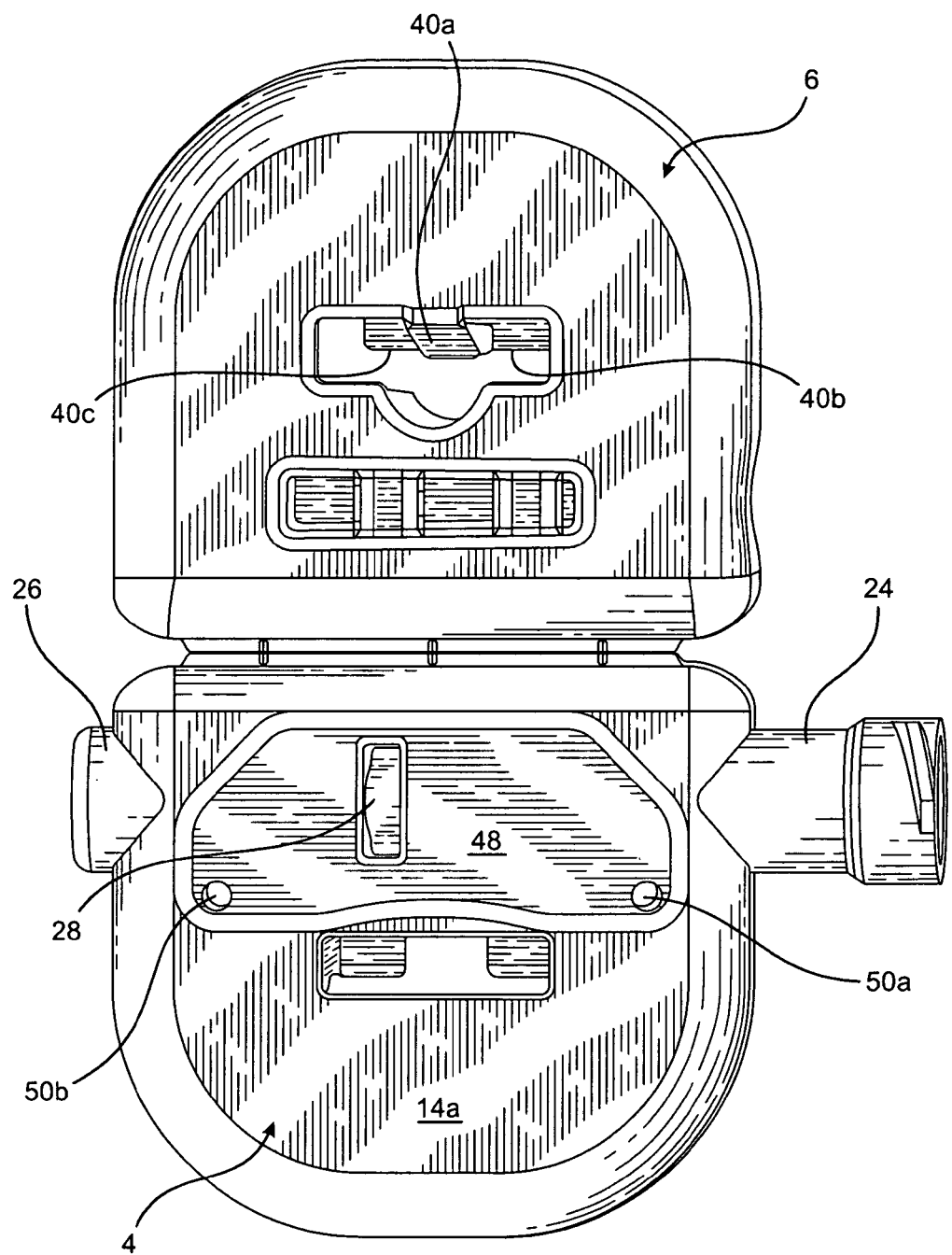
FIG. 6 is a perspective view of the outer surfaces of the two shells of the instant invention medical device before the injection molding process of forming the flexible tubing in the device.

To couple shells 4 and 6 in a locking relationship, integrally extending from inner surface 16b of shell 6 is another latch mechanism in the form of a latch finger 40 interrupted at its middle by a boss 40a (FIGS. 1 and 5) so that finger 40 may be considered to be divided into gripping finger portions 40b and 40c (FIGS. 5 and 6).

With latch mechanisms 34 and 40 in cooperation, when shells 4 and 6 are folded along living hinge 8 so that their respective inner surfaces 14b and 16b face each other, with latch finger 40 snap fitted to catch 34, the adapter device 2 of the instant invention becomes a closed clam shell shaped container, per shown in FIG. 3, with the catheter 32 inserted along flexible tube 30 via aperture end 26 being fixedly held or retained to flexible tubing 30 by retainer structure 38 of shell 6. A fluid through path or passageway is thereby established between luer end 24 and catheter 32.

Figure 4:
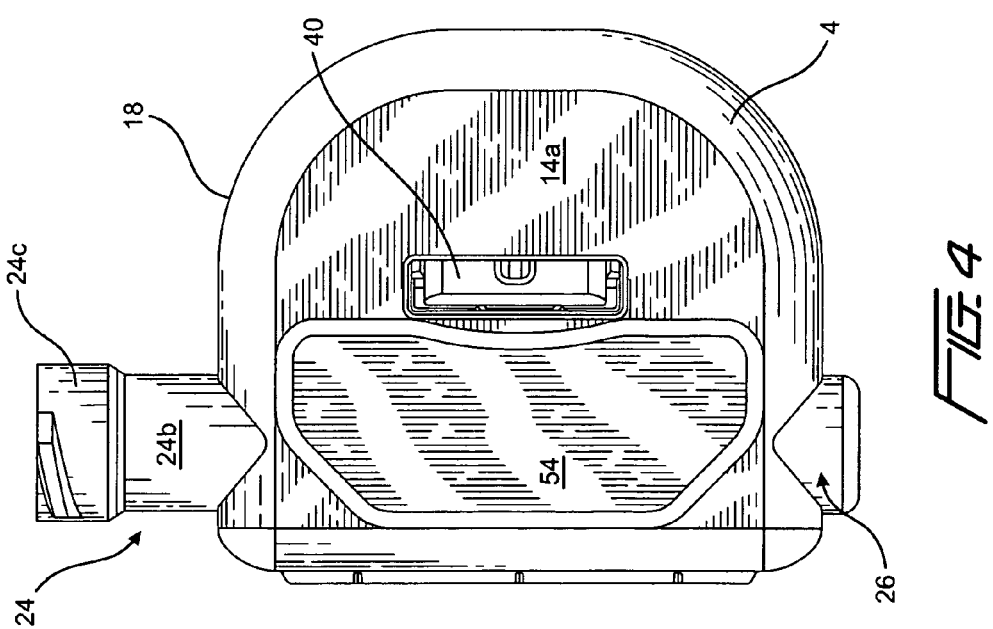
FIG. 4 is a plan view of the outer surface of the one shell of the device of the instant invention having an elastomeric pad and an opening exposing the catch latch mechanism of the device.

As shown in FIGS. 3-5, as the latch mechanisms 34 and 40 are located in the interior of the closed clam shell shaped device, they are therefore remotely located from the respective outer surfaces 14a and 16a of shells 4 and 6 of adapter device 2. Moreover, as each of latch mechanisms 34 and 40 is located at approximately the center of its corresponding shells 4 and 6, latch mechanisms 34 and 40 are also located remotely from the peripheries 4a and 6a of shells 4 and 6. As a result, once engaged in a locking relationship, the latch mechanisms 34 and 40 are not exposed to the environment, and therefore could not easily be tampered with, or be accidentally disengaged and/or uncoupled from each other.

So that shells 4 and 6 could be uncoupled from each other, a disengagement or decouple through hole or notch 42 is provided at outer surface 16a of shell 6 to enable a direct view into exposed latch finger 40, which is in a locking relationship with catch 34. A pointed object such as the male slip end of a syringe may be inserted into notch 42 to press against boss 40a to force latch finger 40 away from catch 34 (specifically catch members 34a and 34b), thereby uncoupling shells 4 and 6 from each other. Once shells 4 and 6 are uncoupled or disengaged from each other, flexible tube 30 is no longer pressedly held by retainer structure 38. Accordingly, catheter 32 can be removed from flexible tubing 30.

To supply medicament to a patient who has a catheter such as catheter 32 inserted in her, assuming that catheter 32 has been inserted into and extends along flexible tubing 30 and shells 4 and 6 of device 2 are lockingly coupled so that catheter 32 is fixedly retained in device 2, a fluid store such as a syringe 46 with a luer end 46a may be threadedly mated to luer 24c of luer end 24 so that the medicament in syringe 46 may be conveyed to catheter 32 and from there delivered to the patient. For the instant invention, luer end 24 may be a conventional luer that is adapted to mate with a conventional counter luer of a conventional syringe, such as 46a shown in FIG. 3. For syringes or fluid lines that are specially designed to have a particular configuration or dimension, luer end 24 could be similarly configured to mate with those specially designed fluid delivery and storage devices.

As discussed above, flexible tubing 30 is formed by the injection molding of an elastomeric material through bore 28 of shell 4. As best shown in FIG. 6, there is a shallow pond or cavity 48 formed on outer surface 14a which, in addition to main bore 28 also has smaller bores 50a and 50b. During the injection process, the elastomeric material is injected though bore 28 (with the appropriate die in opposed relationship to inner surface 14b) to form the flexible tubing 30 between luer fitting end 24 and aperture end 26 in the mold space 50 at the inner surface 14b of shell 4, per shown in FIG. 7. An appropriate journal or pin-like rod extending between luer fitting end 24 and aperture end 26 effects the through passageway for flexible tubing 30 during the injection molding process.

In addition to flexible tubing 30, during the injection molding process, the elastomeric material also forms a flexible elastomeric pad 54 at shallow pond 48 flush with the outer surface 14b of shell 4. The thus formed elastomeric pad 54, anchored to bores 50a and 50b, in addition to possibly having some indicia for example the name of the assignee embossed thereon, provides the user with a touch responsive elastomeric pad for better grasping device 2. Thus, the injection molding of an elastomeric material to shell 4 not only forms the flexible tubing 30 at inner surface 14b of shell 4, it also forms a soft elastomeric finger pad 54 at outer surface 14a of shell 4.

Figure 8:
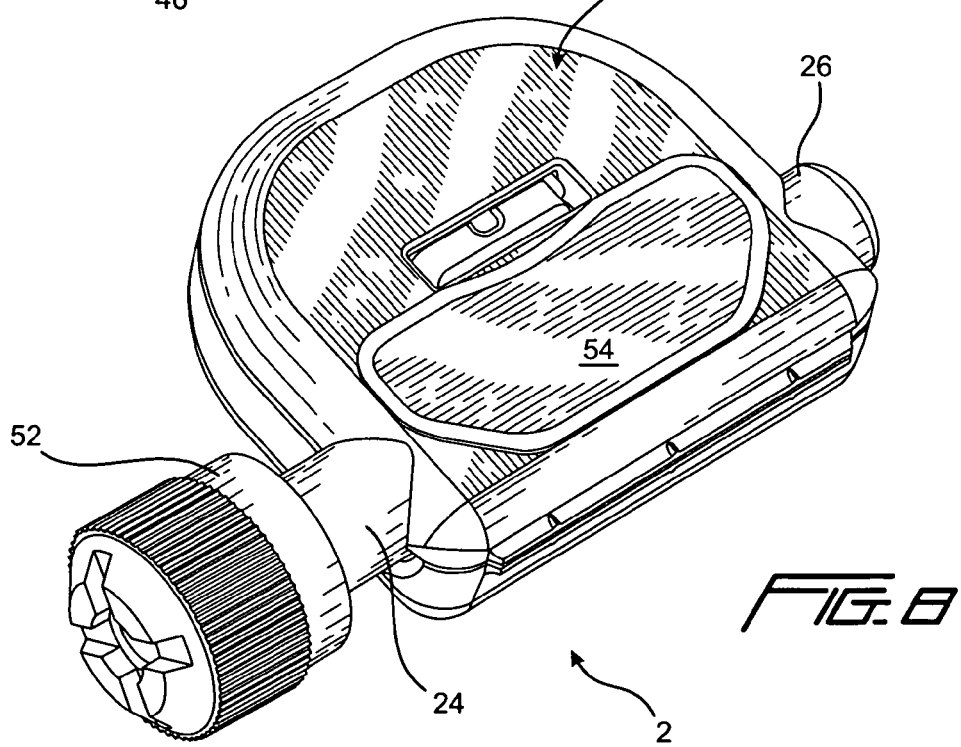
FIG. 8 shows in perspective a locked device of the instant invention with its luer end protected by a protective cover cap.

To provide sterility for the luer end 24, a protective cover cap 52 may be threadedly mated to luer end 24 of the device, per shown in FIGS. 8-10.

Although the adapter device of the instant invention is disclosed for use with an epidural catheter, it should be appreciated that the adapter device as disclosed could also be used for other types of catheters by merely changing the diameter of the aperture end, i.e., the catheter connection port. So, too, although the luer end described is a conventional luer that is adapted to be used with a conventional counterpart luer, the dimensions of the luer end may be varied to mate with fittings of special configurations and dimensions to establish a fluid path between the fluid delivery, transfer or storage device and the catheter. Thus, inasmuch as the present invention is subject to many variations, modifications and changes in detail, it is intended that the matter described throughout this specification and shown in the accompanying drawings be interpreted as illustrative only and not in a limiting sense. Accordingly, it is intended that the invention be limited only by the spirit and scope of the hereto appended claims.

The invention claimed is:

1. A catheter device, comprising one and other shells each having an inner surface and an outer surface, said one and other shells integrally connected at a common hinge and having respective matching peripheries to form a clam shell shaped member, said one shell having formed thereat a luer end and an aperture end communicatively connected by a flexible tubing at said one shell's inner surface so that a through passage is established between said luer end and said aperture end, said aperture end adapted to accept a catheter input to said flexible tubing, said one shell and said other shell each having a center at their respective inner surfaces, said one shell having one latch mechanism at approximately the center of said one shell's inner surface, said other shell having other latch mechanism at approximately the center said other shell's inner surface, said one and other latch mechanisms lockingly engage to couple said one and other shells to each other when said one and other shells are folded along the common hinge to move the respective inner surfaces of said one and other shells to face each other with said one and other latch mechanisms both inside the closed clam shell shaped member, said other shell including an inner surface retainer structure that presses against said flexible tubing to fixedly hold the catheter when said one and other shells are coupled to each other.

2. The catheter device of claim 1, wherein said one and other latch mechanisms at said one and other shells are remotely located from the respective outer surfaces and peripheries of said one and other shells.

3. The catheter device of claim 1, wherein one of said one and other latch mechanisms comprises at least one finger and the other of said one and other latch mechanisms comprises a catch, said at least one finger and said catch each extending from the inner surface of one of said one and other shells to couple said one and other shells to each other when said one and other shells are folded relatively toward each other and their peripheries matchingly abut, a notch formed at the outer surface of the one or other shell having said at least one finger allowing a pointed object to be inserted therein to disengage said at least one finger from said catch to thereby uncouple said one and other shells from each other.

4. The catheter device of claim 1, wherein said luer end and said aperture end are in axial alignment with each other, said flexible tubing joining said luer and aperture ends extending in parallel to the common hinge along an axis offset from the center of said one shell.

5. The catheter device of claim 1, wherein said flexible tubing is formed from an elastomeric material injection molded through at least one bore connecting the outer surface and the inner surface of said one shell, the elastomeric material further forming an elastomeric pad at the outer surface of said one shell.

6. The catheter device of claim 1, wherein said retainer structure comprises an elongated surface that substantially matches said flexible tubing exposed at the inner surface of said one shell, said retainer structure comprising a ribbed surface that includes at least one pair of spaced protrusions orthogonal to said retainer structure that presses against said flexible tubing to form fittedly retain the catheter inside said flexible tubing when said one and other shells are coupled to each other.

7. The catheter device of claim 1, wherein said luer end is adapted to matingly secure the catheter device to a fluid store or a fluid line having a counterpart luer so that a fluid path is established from the fluid store or fluid line to the catheter held by the catheter device.

8. An adapter for coupling a catheter to a fluid store or a fluid line, comprising: a one piece clam shell shaped member having one shell and other shell integrally attached to and foldable toward each other by a living hinge, said one shell and said other shell each have an inner surface and an outer surface, said one shell having formed thereat a luer end and an aperture end connected by a flexible tubing at said one shell's inner surface so that a through passage is established between said luer end and said aperture end, said aperture end adapted to accept the catheter input to said flexible tubing, said one shell and said other shell each having a center at their respective inner surfaces, one latch mechanism at approximately the center of the inner surface of said one shell lockingly engaging other latch mechanism at approximately the center of the inner surface of said other shell when said one and other shells are folded along the living hinge to close upon each other so that said one and other latch mechanisms are located inside the closed clam shell shaped member, a retainer structure at the inner surface of said other shell pressing against said flexible tubing to fixedly hold the catheter when said one and other latch mechanisms are engaged to each other.

9. The adapter of claim 8, wherein said one and other shells have matching peripheries so that said one and other shells, when lockingly coupled to each other, form the clam shell shaped member with a common periphery.

10. The adapter of claim 9, wherein said one and other latch mechanisms at said one and other shells are remotely located from the respective outer surfaces and peripheries of said one and other shells so that when said one and other shells are lockingly coupled to each other, said one and other latch mechanisms are internal to the adapter.

11. The adapter of claim 8, wherein one of said one and other latch mechanisms comprises at least one finger and the other of said one and other latch mechanisms comprises a catch, said at least one finger and said catch each extending from the inner surface of one of said one and other shells to couple said one and other shells to each other when said one and other shells are folded relatively toward each other until said at least one finger and said catch engage, a notch formed at the outer surface of the one or other shell having said at least one finger allowing a pointed object to be inserted therein to disengage said at least one finger from said catch to thereby uncouple said one and other shells from each other.

12. The adapter of claim 8, wherein said luer end and said aperture end are in axial alignment with each other, said flexible tubing joining said luer and aperture ends extending in parallel to the living hinge along an axis offset from the center of said one shell.

13. The adapter of claim 8, wherein said flexible tubing is formed from an elastomeric material injection molded through a bore connecting the outer surface and the inner surface of said one shell, the elastomeric material further forming an elastomeric pad at the outer surface of said one shell.

14. An apparatus comprising:
a catheter;
a fluid store means;
an adapter including a one piece clam shell shaped member having one shell and other shell integrally attached to and foldable toward each other by a living hinge, said one shell and said other shell each have an inner surface and an outer surface, said one shell having formed thereat a luer end and an aperture end connected by a flexible tubing at said one shell's inner surface so that a through passage is established between said luer end and said aperture end, said aperture end for accepting the catheter into said flexible tubing and said luer end for mating with a counterpart luer at said fluid store means, said one shell and said other shell each having a center at their respective inner surfaces, one latch mechanism at approximately the center of the inner surface of said one shell lockingly engaging other latch mechanism at approximately the center of the inner surface of said other shell when said one and other shells are folded along the living hinge to close upon each other so that said one and other latch mechanisms are located inside the closed clam shell shaped member, a retainer structure at the inner surface of said other shell pressing against said flexible tubing to fixedly hold the catheter when said one and other latch mechanisms are engaged to each other;
whereby a fluid path between said catheter and said fluid store means is established by said adapter.

15. The apparatus of claim 14, wherein said catheter comprises an epidural catheter for use in an epidural procedure.

16. The apparatus of claim 14, wherein said one and other shells have matching peripheries so that said one and other shells, when lockingly coupled to each other, form the clam shell shaped member with a common periphery.

17. The apparatus of claim 16, wherein said one and other latch mechanisms at said one and other shells are remotely located from the respective outer surfaces and peripheries of said one and other shells so that when said one and other shells are lockingly coupled to each other, said one and other latch mechanisms are internal to the adapter.

18. The apparatus of claim 14, wherein one of said one and other latch mechanisms comprises at least one finger and the other of said one and other latch mechanisms comprises a catch, said at least one finger and said catch each extending from the inner surface of one of said one and other shells to couple said one and other shells to each other when said one and other shells are folded relatively toward each other until said at least one finger and said catch engage, a notch formed at the outer surface of the one or other shell having said at least one finger allowing a pointed object to be inserted therein to disengage said at least one finger from said catch to thereby uncouple said one and other shells from each other.

19. The apparatus of claim 14, wherein said luer end and said aperture end are in axial alignment with each other, said flexible tubing joining said luer and aperture ends extending in parallel to the living hinge along an axis offset from the center of said one shell.

20. The apparatus of claim 14, wherein said flexible tubing is formed from an elastomeric material injection molded through a bore connecting the outer surface and the inner surface of said one shell, the elastomeric material further forming an elastomeric pad at the outer surface of said one shell; and
wherein said retainer structure comprises a ribbed surface to form fittedly press onto said flexible tubing when said one and other latch mechanisms are engaged to each other.

* * * * *